United States Patent [19]

Iglesias

[11] 4,030,502

[45] June 21, 1977

[54] ANTI-ARCING RESECTOSCOPE

[76] Inventor: Jose Juan Iglesias, 1341 North Avenue, Elizabeth, N.J. 07200

[22] Filed: Dec. 5, 1975

[21] Appl. No.: 638,061

[52] U.S. Cl. .................................. 128/303.15
[51] Int. Cl.² ................................. A61B 17/32
[58] Field of Search ............... 128/303.15, 303.13, 128/303.14, 303.16, 303.17

[56] References Cited

UNITED STATES PATENTS

| 2,102,270 | 12/1937 | Hyams | 128/303.17 |
|---|---|---|---|
| 3,850,175 | 11/1974 | Iglesias | 128/303.15 |
| 3,939,839 | 2/1976 | Curtiss | 128/303.15 |
| 3,939,840 | 2/1976 | Storz | 128/303.15 |

Primary Examiner—Robert W. Michell
Assistant Examiner—Lee S. Cohen
Attorney, Agent, or Firm—Scrivener Parker Scrivener and Clarke

[57] ABSTRACT

A resectoscope used in performing transurethral operations has a telescope extending longitudinally of the instrument which is supported and stabilized by an elongated metallic tube which at its proximate end is fixed to the block of the instrument. In accordance with the invention the distal end of the tube is extended beyond the distal end of the telescope sufficiently that there will be no interference with illumination through the telescope but electrical arcing between the bare wire of the cutting loop of the instrument and the telescope will be prevented. The tube extension may be made of metal or of a material which is electrically nonconductive.

4 Claims, 4 Drawing Figures

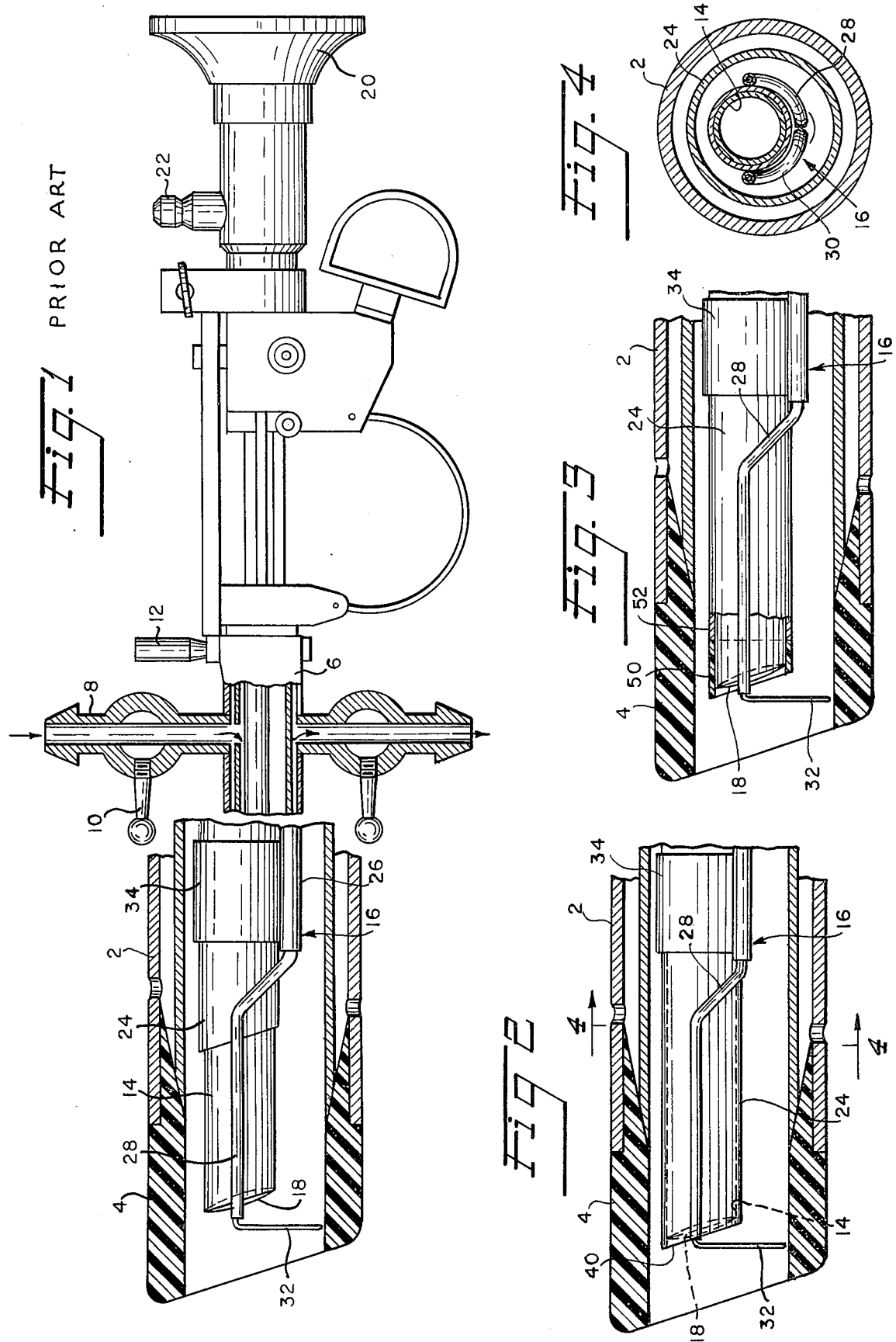

ANTI-ARCING RESECTOSCOPE

BACKGROUND OF THE INVENTION

A resectoscope having parts of conventional construction is disclosed in FIG. 1 as background for disclosure of the invention, and comprises a metallic tubular sheath 2 which provides a passageway through the human urethra to the area of visual and operative interest, and which has at its distal end a beak 4 which is formed of an electrically insulating material such as a synthetic plastic. At its proximate end the sheath is attached to a metallic block 6 at which there is a tube 8 with stopcock 10 for the introduction of clear irrigating fluid, and a thumb screw 12 for attaching the sheath's metallic socket to the block 6 which activates the cutting loop assembly and electrode in performing an operation.

Within the sheath are the telescope 14 and the cutting loop assembly 16. The telescope has an objective lens 18 at its distal end and an ocular lens (not shown) and eyepiece 20 at its proximal end. Fiberglass light conductors (not shown) extend through the telescope from an external connection 22 to the distal end for providing illumination. The telescope is supported and stabilized within the sheath by an elongated metallic tube 24 which partially or entirely surrounds the telescope in tight engagement. This tube is connected at its proximal end to the block 6 and in all resectoscopes prior to this invention its distal end is positioned proximal to the distal end of the telescope.

The cutting loop assembly 16 comprises, in one of its conventional forms, the elongated hollow stem 26 which extends along and beneath the telescope stem and from the distal end of which there protrude two parallel arms 28, 30 which are insulated wires positioned on opposite sides of the telescope adjacent its distal end and which are connected at their distal ends by a depending semi-circular bare wire cutting loop 32 which is activated by high frequency electrical energy and is used to resect pathological tissues and coagulate bleeding vessels. The stem 26 transmits the reciprocating movement of the working element to the cutting loop 32, and the wire in the stem and arms 28, 30 transmits high frequency electrical energy to the cutting loop 32. A tube 34 is connected to the distal end of the stem 26, and is positioned above the stem, and slidably surrounds the tube 24 in order to provide support to the cutting loop 16.

In performing an operative procedure using the resectoscope, electrical arcing between the un-insulated distal ends of the arms or the upper ends of the cutting loop and the adjacent distal end of the telescope often occurs when the cutting loop assembly is moved to rest position and the end of the telescope is touched by a piece of resected tissue which has adhered to the cutting loop or by the wire of a broken or deformed cutting loop. This arcing may damage the telescope, adversely affect the operative procedure and injure the surgeon. There have been many reports in the literature of eye injury to surgeons while performing transurethral operations, and it is well known that most surgeons have experienced electrical shocks and burning of the hand, cheek, nose and ears caused by arcing during performance of an operation with the use of a resectoscope. Among the methods suggested to correct this difficulty are (1) positioning the distal end of the telescope backward within the sheath beyond the position of optimum vision, (2) reducing the proximal movement of the cutting loop assembly in order to maintain the bare wire cutting loop at a safe distance from the telescope, and (3) extending the insulation of the spaced parallel arms of the cutting loop assembly over and beyond the junction of the arms and depending loop. None of these have been satisfactory as none have completely prevented arcing, and the object of my present invention has been to prevent arcing while at the same time maintaining the increased illumination and field of vision provided by modern telescopes of resectoscopes, without interference with the endoscopic field of vision and without decreasing the capacity of resection at each stroke of the cutting loop.

SUMMARY OF THE INVENTION

In a resectoscope the metal tube which partially or completely surrounds the telescope and supports and stabilizes it is extended at its distal end beyond and distal end of the telescope whereby electrical arcing between the bare wire cutting loop and the telescope tube will be diverted to the distal end of the tube and will not reach the telescope. In another embodiment at least the distal end of the tube is made of a material which is non-conductive to electricity and is extended beyond the distal end of the telescope by such a distance that it engages the bare wire cutting loop in its movement to rest position and prevents the bare wire cutting loop from coming within arcing distance of the metal telescope tube.

DESCRIPTION OF THE DRAWINGS

FIG. 1 is a side view of a resectscope, being partially broken away and partially in section and enlarged to illustrate the prior art and the problems to which the present invention is addressed;

FIG. 2 shows parts of the resectoscope illustrated in FIG. 1 as modified by the present invention;

FIG. 3 is similar to FIG. 2 and illustrates a second form the invention may take, and FIG. 4 is a sectional view taken on line 4—4 of FIG. 2.

DESCRIPTION OF THE INVENTION

In the preferred embodiment of the invention which is disclosed in FIG. 2 the tube 24 which supports and stabilized the telescope tube is made entirely of metal and is of such length that its distal end 40 is distal to the distal end of the telescope tube. In this condition and position any electrical arcing from the bare wire cutting loop 32 to the distal end of the metallic telescope tube will be diverted to the distal end 40 of the tube 24 and will not reach the telescope. The extension of the distal end of the tube beyond the distal end of the telescope in accordance with the invention should be as great as possible without interference with the illumination and field of vision of the telescope, and should be at least 0.5 mm. but may be greater if permitted by the angular extent of the field of vision.

In a second embodiment of the invention, which is disclosed in FIG. 3, at least the distal end 50 of the tube 24 which supports and stabilized the telescope is made of material which is non-conductive of electricity and this end is of such a length and is extended beyond the distal end of the telescope tube by such a distance that when the cutting loop assembly is in its rest position the bare wire cutting loop will engage the distal end of the tube and will be held away from the metallic part 52 of the telescope by such a distance that arcing involving the telescope cannot occur at the voltage and current being used. If only the distal end of the tube is formed of non-conductive material the remainder of the tube may be formed of conductive material, but in this case the non-conductive part at the distal end must be of sufficient length that the conductive parts of the telescope and tube are sufficiently spaced from the bare wire cutting loop in its rest position that arcing between the loop and the distal end of the metal parts of the telescope and tube will not take place at the current and voltage being used.

I claim:

1. A resectoscope comprising a sheath having a beaked distal end, a telescope within and extending longitudinally of the sheath and having a distal end having a lens adjacent the beaked distal end of the sheath, a tube extending longitudinally of the sheath and the telescope and engaging and at least partially surrounding the telescope to support and stablize it, the tube having a distal end adjacent the distal end of the telescope, a cutting loop assembly adjacent and extending longitudinally of the telescope and having a depending bare wire loop which is positioned distal to the distal end of the telescope and is adapted to be charged with electricity, means for reciprocating the cutting loop assembly to move the bare wire loop toward and away from the distal end of the telescope, the distal end extremity of the tube being positioned distally of the distal end of the telescope and proximally of the most proximal position of the bare wire loop to prevent electrical arcing between the bare wire loop and the distal end of the telescope.

2. A resectoscope according to claim 1, in which the distal end of the tube is metallic whereby arcing is diverted to the tube and by-passes the telescope.

3. A resectoscope according to claim 2, in which the tube extends at least 0.5 mm. beyond the distal end of the telescope.

4. A resectoscope according to claim 1, in which at least the distal end of the tube is formed of material which is non-conductive to electricity and the non-conductive part extends beyond the distal end of the telescope by a sufficient distance and is of sufficient length that arcing between the bare wire cutting loop and the telescope and between the bare wire cutting loop and the remainder of the tube cannot occur at the current and voltage being used.

* * * * *